United States Patent
Botzer (10) Patent No.: US 11,779,770 B2
(45) Date of Patent: Oct. 10, 2023

(54) UNIVERSAL PACING OF A CATHETER

(71) Applicant: Biosense Webster (Israel) Ltd., Yokneam (IL)

(72) Inventor: Lior Botzer, Timrat (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 92 days.

(21) Appl. No.: 16/938,200

(22) Filed: Jul. 24, 2020

(65) Prior Publication Data

US 2022/0023642 A1 Jan. 27, 2022

(51) Int. Cl.
*A61N 1/37* (2006.01)
*A61M 25/00* (2006.01)
*A61M 25/10* (2013.01)

(52) U.S. Cl.
CPC ....... *A61N 1/3706* (2013.01); *A61M 25/0012* (2013.01); *A61M 25/10* (2013.01); *A61N 1/3702* (2013.01); *A61N 1/3716* (2013.01); *A61M 2210/125* (2013.01)

(58) Field of Classification Search
CPC .. A61N 1/3706; A61N 1/3702; A61N 1/3716; A61M 25/0012; A61M 25/10; A61B 5/6853
See application file for complete search history.

(56) References Cited

U.S. PATENT DOCUMENTS

| | | |
|---|---|---|
| 5,174,289 A | 12/1992 | Cohen |
| 2002/0010392 A1 | 1/2002 | Desai |
| 2002/0183638 A1 | 12/2002 | Swanson |
| 2005/0256521 A1 | 11/2005 | Kozel |
| 2012/0004564 A1 | 1/2012 | Dobak, III |
| 2015/0306410 A1 | 10/2015 | Marshall et al. |
| 2016/0278657 A1 | 9/2016 | Narayan et al. |
| 2017/0245774 A1 | 8/2017 | Narayan et al. |
| 2019/0298213 A1* | 10/2019 | Niederer ............ A61B 5/35 |

OTHER PUBLICATIONS

International Search Report and Written Opinion dated Nov. 11, 2021 for PCT International Application No. PCT/IB2021/055474.

* cited by examiner

*Primary Examiner* — Tammie K Marlen
(74) *Attorney, Agent, or Firm* — Volpe Koenig (57) ABSTRACT

A method is provided. The method includes pacing, by electrodes of a catheter, a heart tissue with pulses. The method includes observing, by the electrodes, a period of electrophysiological repolarization for the heart tissue. The period of electrophysiological repolarization is caused by the pacing. The method also includes measuring, by the electrodes, an electrical signal within the heart tissue after the period of electrophysiological repolarization.

18 Claims, 6 Drawing Sheets

UNIVERSAL PACING OF A CATHETER

FIELD OF INVENTION

The present invention is related to signal processing and, more particularly, to universal pacing by a catheter to enable improved cardiac signal analysis.

BACKGROUND

Treatments for cardiac conditions, such as cardiac arrhythmia, often require analyzing a specific region or focal point of heart tissue via pacing. Pacing is a technique used in Electrophysiology for variety of reasons, such as identifying critical conduction path, interrogation of tissue viability, controlling and overtaking the cardiac rhythm, confirmation of block, detection of gaps, and identification of possible arrhythmia sources. Pacing is administrated using catheter electrodes to provide a very short pulse of electrical current to activate tissue in a given region and generate an electric wave from a particular point.

Currently, pacing is performed either as unipolar pacing (one source electrode and one returned distant larger electrode) or more often bipolar pacing (between two adjacent electrodes). However, there are presently no techniques that uses multiple electrodes concurrently for pacing (whether concurrent bipolar pacing from multiple electrodes or from multiple electrodes to single larger electrode). Following such a maneuver, it would be possible to synchronize a large tissue area (under the pacing electrodes) and to establish the conduction pattern under the electrodes following the refractory period of that tissue. For example, such a technique may be beneficial for identifying focal sources in this area.

SUMMARY

According to an embodiment, a method is provided. The method includes pacing, by electrodes of a catheter, a heart tissue with pulses. The method includes observing, by the electrodes, a period of electrophysiological repolarization for the heart tissue. The period of electrophysiological repolarization is caused by the pacing. The method also includes measuring, by the electrodes, an electrical signal within the heart tissue after the period of electrophysiological repolarization.

According to one or more embodiments, the method embodiment above can be implemented as an apparatus, a system, and/or a computer program product.

BRIEF DESCRIPTION OF THE DRAWINGS

A more detailed understanding may be had from the following description, given by way of example in conjunction with the accompanying drawings, wherein like reference numerals in the figures indicate like elements, and wherein.

DETAILED DESCRIPTION

Disclosed herein is cardiac pacing and diagnosis apparatus utilizing pacing by all electrodes of a catheter (e.g., a mapping catheter) at one time to generate a period of simultaneous activation of a patch of tissue having direct contact with electrodes of the catheter. In an embodiment, pacing is used in atrial fibrillation (AFIB) to observe the electrocardiograph (ECG) intracardiac signals immediately following a termination of pacing artifacts (e.g., 20 ms to 30 ms pending the current used). In another embodiment, pacing is used to understand if there is a source in an area where the pacing occurred. The cardiac pacing and diagnosis apparatus includes a processor executable code or software that is necessarily rooted in process operations by, and in processing hardware of, medical device equipment to provide a method for analyzing a specific region or focal point of heart tissue in response to the pacing. According to an embodiment, the cardiac pacing and diagnosis apparatus provides specific pacing and capturing operations that involve a multi-step manipulation of electrical signals with respect to the heart tissue to understand an electrophysiology of the heart tissue with more precision.

In this regard and in operation, the cardiac pacing and diagnosis apparatus controls pacing of a heart tissue region from multiple electrodes of a catheter. For instance, each of the electrodes provides a pulse, at the same time, at one particular, isolated region. This pacing generates a period of electrophysiological repolarization for the heart tissue region and a refractory period of tissue underneath the heart tissue region. After this period of electrophysiological repolarization, the cardiac pacing and diagnosis apparatus utilizes the multiple electrodes to measure where a first electrical signal begins within the heart tissue region. The cardiac pacing and diagnosis apparatus further utilizes the multiple electrodes to measure a progress of returning activity patterns (e.g., coming from within the electrode or from the boundary or both) in the heart tissue region to isolate and analyze possible focal points of interest.

For example, when a heart is in tachycardia (e.g., a condition that makes the heart beat more than 100 times per minute), physicians want to inspect a specific area for an existence of source. The problem facing the physicians (with respect to AFIB) is that this area is constantly bombarded by activity coming from various directions. When pacing from an electrode, the captured tissue (if the pacing is successful) propagates throughout the heart. Normal conduction velocity for healthy tissue is about 0.7 mm per ms and for an unhealthy heart it is much lower. This means that over a catheter of 15 mm across, a time to spread the signal would be 20 ms from side to the next. Importantly, the tissue would be activated gradually, which is similar for a sinus rhythm or a focal source. Alternatively, if the pacing at one time captures tissue, which would be activated together, then this extra 20 ms of propagation along the catheter is saved. Note that, once pacing is terminated and tissue has depolarized, each cell will start to repolarize at its own pace. The 20 ms window provide a longer time for inspection, regardless of whether a source of the tachycardia is coming from within or from outside the electrode coverage. In AFIB, a recovery time can be between 75 ms to 200 ms; therefore, having at least 20 ms more of inspection time is important. If the source is coming from within and not from the boarder, this is taken as an indication that the tissue under the electrode is generating source that may be treated. If not, it is still undetermined as to whether the wave coming from the outside could have prevented the activation of the tissue under the electrodes.

The technical effects and benefits of the cardiac pacing and diagnosis apparatus include providing cardiac physicians and medical personnel a way to observe how a specific focal point of the heart tissue responds after pacing. Thus, the cardiac pacing and diagnosis apparatus particularly utilizes and transforms a catheter and medical device equipment to enable/implement pacing procedures and signal analysis that are otherwise not currently available or currently performed by cardiac physicians and medical personnel.

Figure 1:
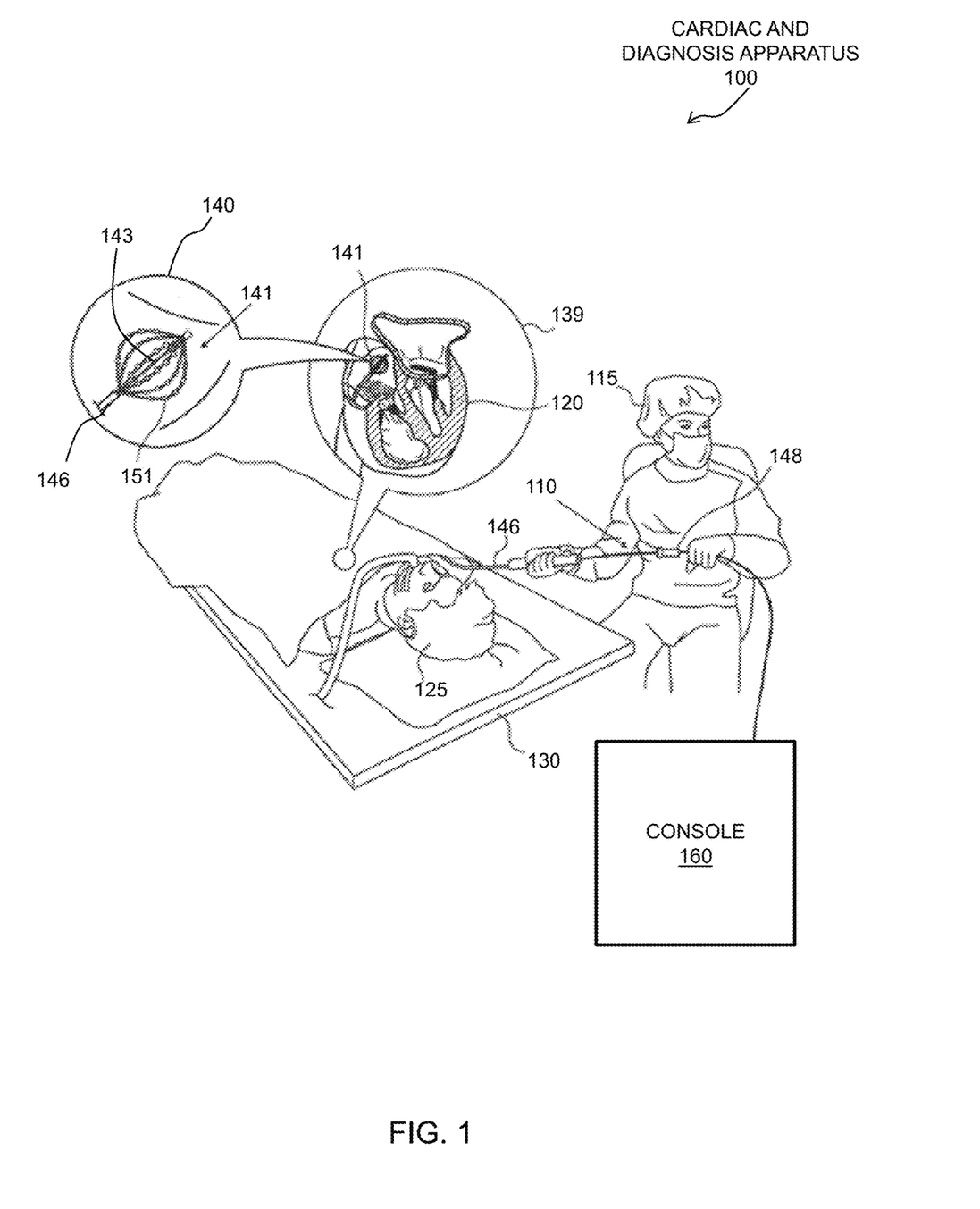
FIG. 1 illustrates a diagram of a cardiac pacing and diagnosis apparatus in which one or more features of the disclosure subject matter can be implemented according to one or more embodiments.

FIG. 1 is a diagram of a cardiac pacing and diagnosis apparatus 100 in which one or more features of the disclosure subject matter can be implemented according to one or more embodiments. The cardiac pacing and diagnosis apparatus 100 can generally referred to as medical device equipment. All or parts of the cardiac pacing and diagnosis apparatus 100 may be used to collect biometric data via universal pacing operations and/or all or parts of system 100 may be used to implement cardiac pacing and diagnosis software described herein.

The cardiac pacing and diagnosis apparatus 100 includes a probe 110, having shafts that may be navigated by a physician or a medical professional 115 into a body part, such as a heart 120, of a patient 125 lying on a bed (or a table) 130, as shown in an insert 139. According to exemplary embodiments, multiple probes may be provided; however, for purposes of conciseness, a single probe 110 is described herein. Yet, it is understood that the probe 110 may represent multiple probes. An inset 140 shows an enlarged view a first end of the probe, inside a cardiac chamber of the heart 120. The probe 110, as shown in insert 140, includes a catheter 141 (e.g., a mapping catheter), a shaft 143, and a sheath 146. The probe 110 also includes a manipulator 148 and is connected to (in communication with) a console 160 storing and executing the cardiac pacing and diagnosis software therein.

According to embodiments, the medical professional 115 may insert the shaft 143 through the sheath 146, while manipulating a distal end of the shaft 143 using the manipulator 148 near the proximal end of the catheter 141 and/or deflection from the sheath 146. As shown in the inset 140, the catheter 141 may be fitted at the distal end of the shaft 143. The catheter 141 may be inserted through the sheath 146 in a collapsed state and may be then expanded within the heart 120. The catheter 141 includes one or more elements (e.g., at least one electrode 151).

In accordance with one or more embodiments, the catheter 141 can be of any shape or type that includes one or more elements that are used to implement the embodiments disclosed herein. Note that the one or more elements may be any elements configured to pace, to ablate, and/or to collect biometric data. More particularly, in an embodiment, the one or more elements may be electrodes (e.g., at least one electrode 151), transducers, or one or more other elements. Further, while the catheter 141 is shown to be a point catheter (which includes the at least one electrode 151 and a catheter needle), it will be understood that the catheter 141 is representative of one or more catheters. According to other embodiments, multiple elements may be connected via splines that form the shape of the catheter 141.

Other examples of the catheter 141 include a linear catheter with multiple electrodes, a balloon catheter including electrodes dispersed on multiple spines that shape the balloon, a lasso or loop catheter with multiple electrodes, or any other applicable shape. Linear catheter may be fully or partially elastic such that it can twist, bend, and or otherwise change its shape based on received signal and/or based on application of an external force (e.g., cardiac tissue) on the linear catheter. The balloon catheter may be designed such that when deployed into a patient's body, its electrodes may be held in intimate contact against an endocardial surface. As an example, a balloon catheter may be inserted into a lumen, such as a pulmonary vein (PV). The balloon catheter may be inserted into the PV in a deflated state such that the balloon catheter does not occupy its maximum volume while being inserted into the PV. The balloon catheter may expand while inside the PV such those electrodes on the balloon catheter are in contact with an entire circular section of the PV. Such contact with an entire circular section of the PV, or any other lumen, may enable efficient pacing, mapping, and/or ablating.

In accordance with one or more embodiments, the catheter 141 includes a mesh, balloon, or spoon catheter having a plurality of electrodes. For instance, the mesh, balloon, or spoon catheter can have at least forty electrodes or, in some cases, exactly 48 electrodes.

The catheter 141 may be configured to damage tissue areas of an intra-body organ, such by ablating tissue areas of a cardiac chamber of the heart 120. The catheter 141 may also be further configured to pace with pulses and to observe/obtain biometric data, in response to those pulses. In this regard, the catheter 141 may be positioned within a body of the patient 125 (e.g., within the heart 120) and a position of the catheter 141 may be determined by the console 160 based on signals transmitted and received between the one or more electrodes 151, along with body patches and/or body surface electrodes. The electrodes 151 may further sense the biometric data (e.g., electrical signals of the heart, such as a sinus heart rhythm or sinus rhythm) from within the body of the patient 125 (e.g., within the heart 120). The biometric data may be associated with the determined position of the catheter such that a rendering of the patient's body part (e.g., the heart 120) may be displayed and may show the biometric data overlaid on a shape of the body. Note that the sinus rhythm can be any cardiac rhythm in which depolarisation of a cardiac muscle begins at a sinus node. For example, the sinus rhythm can include a normal heart beat with respect to the heart rate and rhythm (e.g., a human heart rate generally falls between 60 and 100 beats per minute).

In operation, the cardiac pacing and diagnosis apparatus 100 can be utilized to detect, diagnose, and treat cardiac conditions. Cardiac conditions, such as cardiac arrhythmias (atrial fibrillation in particular), persist as common and dangerous medical ailments, especially in the aging population. In patients (e.g., the patient 125) with normal sinus rhythm, the heart (e.g., the heart 120), which is comprised of atrial, ventricular, and excitatory conduction tissue, is electrically excited to beat in a synchronous, patterned fashion (note that this electrical excitement can be detected as intracardiac signals).

In patients (e.g., the patient 125) with cardiac arrhythmias, abnormal regions of cardiac tissue do not follow the synchronous beating cycle associated with normally conductive tissue as in patients with normal sinus rhythm.

Instead, the abnormal regions of cardiac tissue aberrantly conduct to adjacent tissue, thereby disrupting the cardiac cycle into an asynchronous cardiac rhythm (note that this asynchronous cardiac rhythm can also be detected as intra-cardiac signals). Such abnormal conduction has been previously known to occur at various regions of the heart (e.g., the heart 120), for example, in the region of the sino-atrial (SA) node, along the conduction pathways of the atrioventricular (AV) node, or in the cardiac muscle tissue forming the walls of the ventricular and atrial cardiac chambers.

Further, cardiac arrhythmias, including atrial arrhythmias, may be of a multiwavelet reentrant type, characterized by multiple asynchronous loops of electrical impulses that are scattered about the atrial chamber and are often self-propagating (e.g., another example of intracardiac signals). Alternatively, or in addition to the multiwavelet reentrant type, cardiac arrhythmias may also have a focal origin, such as when an isolated region of tissue in an atrium fires autonomously in a rapid, repetitive fashion (e.g., which can be a focal point of interest for the cardiac pacing and diagnosis apparatus 100). Ventricular tachycardia (V-tach or VT) is a tachycardia, or fast heart rhythm that originates in one of the ventricles of the heart. This is a potentially life-threatening arrhythmia because it may lead to ventricular fibrillation and sudden death.

One type of arrhythmia, atrial fibrillation, occurs when the normal electrical impulses generated by the sinoatrial node (e.g., sinus rhythm) are overwhelmed by disorganized electrical impulses that originate in the atria and pulmonary veins causing irregular impulses to be conducted to the ventricles. An irregular heartbeat results and may last from minutes to weeks, or even years. Atrial fibrillation (AF) is often a chronic condition that leads to a small increase in the risk of death often due to strokes. The first line of treatment for AF is medication that either slows the heart rate or revert the heart rhythm back to normal. Additionally, persons with AF are often given anticoagulants to protect them from the risk of stroke. The use of such anticoagulants comes with its own risk of internal bleeding. In some patients, medication is not sufficient and their AF is deemed to be drug-refractory, i.e., untreatable with standard pharmacological interventions. Synchronized electrical cardioversion, which is a procedure in which an electric current is used to reset the heart's rhythm back to a normal sinus rhythm, may also be used to convert AF to a normal heart rhythm.

Herein, the cardiac pacing and diagnosis apparatus 100 provides cardiac physicians and medical personnel a way to observe how a specific focal point of the heart tissue responds after pacing. Thus, the cardiac pacing and diagnosis apparatus 100 particularly utilizes and transforms the catheter 141 and the console 160 to enable/implement pacing procedures and signal analysis that otherwise are not currently available or currently performed by cardiac physicians and medical personnel.

More particularly, the console 160 is connected to and in communication with the probe 110 and the catheter 141. The console 160 may store and execute the cardiac pacing and diagnosis software. According to an embodiment, the console 160 includes at least a processor and a memory, where the processor executes computer instructions with respect to the cardiac pacing and diagnosis software described herein and the memory stores the computer instructions for execution by the processor.

The console 160 can be any computing device comprising software and/or hardware, such as a general-purpose computer, with suitable front end and interface circuits for transmitting and receiving signals to and from the catheter 141, as well as for controlling the other components of system 100. The front end and interface circuits include input/output (I/O) communication interfaces that enables the console 160 to receive signals from and/or transfer signals to the at least one electrode 151. In some embodiments, the console 160 may be further configured to receive biometric data, such as electrical activity, and determine if a given tissue area conducts electricity. According to an embodiment, the console 160 may be located, for example, in the catheter 151, in an external device, in a mobile device, in a cloud-based device, or may be a standalone processor/computer.

As noted above, the console 160 may include a general-purpose computer, which may be programmed in software (e.g., the cardiac pacing and diagnosis software) to carry out the functions of the cardiac pacing and diagnosis apparatus 100 described herein. The software may be downloaded to the general-purpose computer in electronic form, over a network, for example, or it may, alternatively or additionally, be provided and/or stored on non-transitory tangible media, such as magnetic, optical, or electronic memory (e.g., any suitable volatile and/or non-volatile memory, such as random-access memory or a hard disk drive). The example configuration shown in FIG. 1 may be modified to implement the embodiments disclosed herein. The disclosed embodiments may similarly be applied using other system components and settings. Additionally, the cardiac pacing and diagnosis apparatus 100 may include additional components, such as elements for sensing electrical activity, wired or wireless connectors, processing and display devices, or the like.

According to an embodiment, a display is connected to the console 160. During a procedure, the console 160 may facilitate the presentation of a body part rendering to the medical professional 115 on the display, and store data representing the body part rendering in a memory. In some embodiments, the medical professional 115 may be able to manipulate the body part rendering using one or more input devices such as a touch pad, a mouse, a keyboard, a gesture recognition apparatus, or the like. For example, an input device may be used to change a position of the catheter 141, such that rendering is updated. In alternative embodiments, the display may include a touchscreen that can be configured to accept inputs from the medical professional 115, in addition to presenting the body part rendering. Note that the display may be located at a same location or a remote location such as a separate hospital or in separate healthcare provider networks. Additionally, the cardiac pacing and diagnosis apparatus 100 may be part of a surgical system that is configured to obtain anatomical and electrical measurements of a patient's organ, such as the heart 120, and to perform a cardiac ablation procedure. An example of such a surgical system is the Carto® system sold by Biosense Webster.

The console 160 may be connected, by a cable, to body surface electrodes, which may include adhesive skin patches that are affixed to the patient 125. The processor of the console 160, in conjunction with a current tracking module, may determine position coordinates of the catheter 141 inside the body part (e.g., the heart 120) of the patient 125. The position coordinates may be based on impedances or electromagnetic fields measured between the body surface electrodes and the electrode or other electromagnetic components (e.g., the at least one electrode 151) of the catheter 141. Additionally or alternatively, location pads may be located on a surface of bed 130 and may be separate from the bed 130.

The cardiac pacing and diagnosis apparatus 100 may also, and optionally, obtain biometric data such as anatomical measurements of the heart 120 using ultrasound, computed tomography (CT), magnetic resonance imaging (MRI) or other medical imaging techniques known in the art. The cardiac pacing and diagnosis apparatus 100 may obtain ECGs or electrical measurements using catheters (e.g., the catheter 141) or other sensors that measure electrical properties of the heart 120. The biometric data including anatomical and electrical measurements may then be stored in a non-transitory tangible media of the console 160. The biometric data may be transmitted from the non-transitory tangible media to a server, which may be local or remote, using a network as further described herein.

According to one or more embodiments, catheters (e.g., the catheter 141) containing position sensors may be used to determine the trajectory of points on the cardiac surface. These trajectories may be used to infer motion characteristics such as the contractility of the tissue. Maps depicting such motion characteristics may be constructed when the trajectory information is sampled at a sufficient number of points in the heart.

Figure 2:
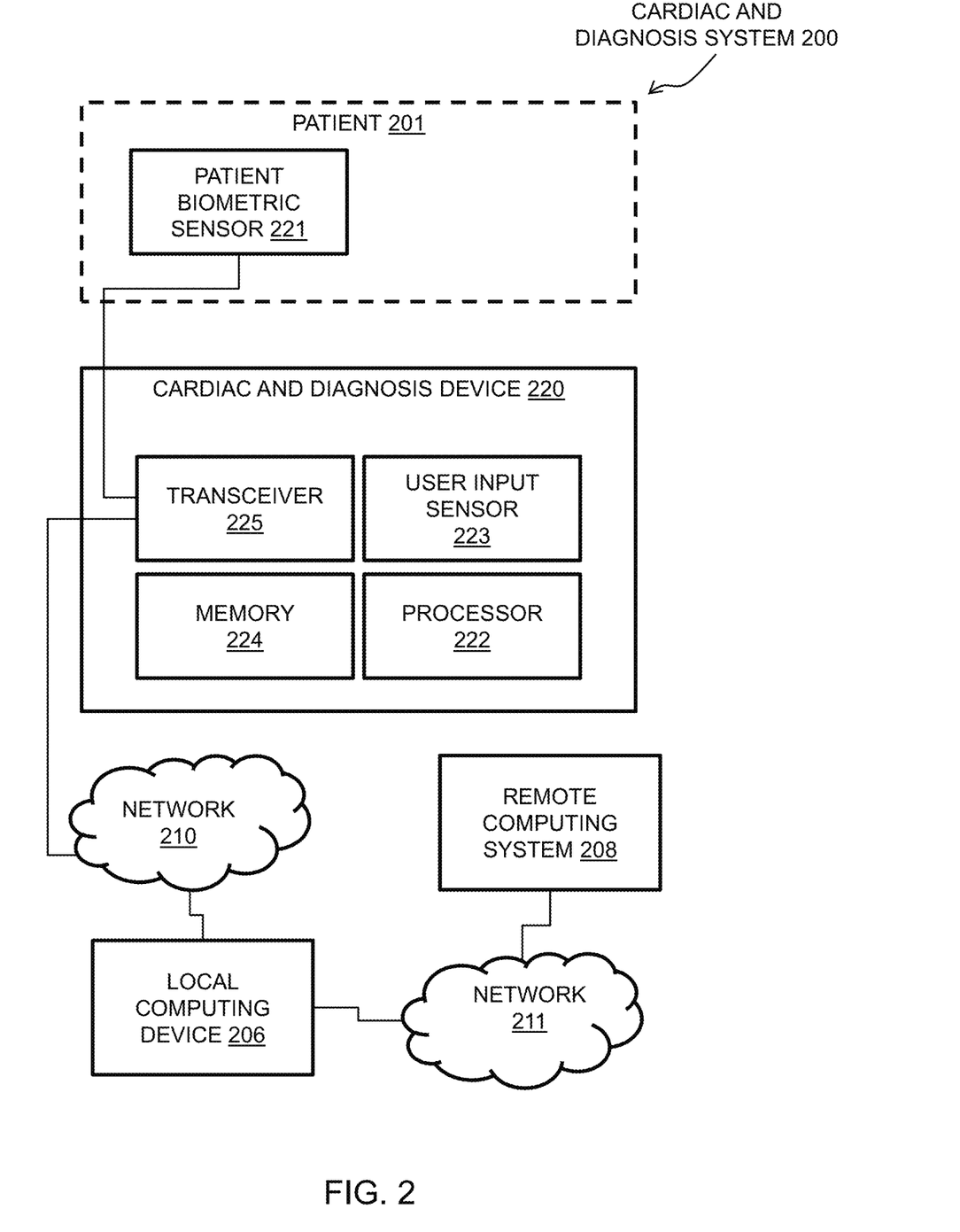
FIG. 2 illustrates a diagram of a cardiac pacing and diagnosis system in which one or more features of the disclosure subject matter can be implemented according to one or more embodiments.

Turning now to FIG. 2, a diagram of a cardiac pacing and diagnosis system 200 in which one or more features of the disclosure subject matter can be implemented is illustrated according to one or more embodiments. The cardiac pacing and diagnosis system 200 includes a patient 201 (e.g., an example of the patient 125 of FIG. 1), a local computing device 206, a remote computing system 208, a first network 210, and a second network 211. Further, a cardiac pacing and diagnosis device 220 can include a patient biometric sensor 221, a processor 222, a user input (UI) sensor 223, a memory 224, and a transmitter-receiver (i.e., transceiver) 225. Note that the patient biometric sensor 221 can be an example of the catheter 141 of FIG. 1, and the cardiac pacing and diagnosis device 220 can be an example of the console 160 of FIG. 1.

The local computing device 206 and/or the remote computing system 208, along with the cardiac pacing and diagnosis device 220, can be any combination of software and/or hardware that individually or collectively store, execute, and implement the cardiac pacing and diagnosis software and functions thereof. Further, the local computing device 206 and/or the remote computing system 208, along with the cardiac pacing and diagnosis device 220, can be an electronic, computer framework comprising and/or employing any number and combination of computing device and networks utilizing various communication technologies, as described herein. The local computing device 206 and/or the remote computing system 208, along with the cardiac pacing and diagnosis device 220, can be easily scalable, extensible, and modular, with the ability to change to different services or reconfigure some features independently of others.

According to an embodiment, the local computing device 206 and the remote computing system 208, along with the cardiac pacing and diagnosis device 220, include at least a processor (e.g., the processor 222 as described herein) and a memory (e.g., the memory 224 as described herein), where the processor executes computer instructions with respect to the cardiac pacing and diagnosis software and the memory stores the computer instructions for execution by the processor.

The local computing device 206 of the cardiac pacing and diagnosis system 200 is in communication with the cardiac pacing and diagnosis device 220 and may be configured to act as a gateway to the remote computing system 208 through the second network 211. The local computing device 206 may be, for example, a smart phone, smartwatch, tablet or other portable smart device configured to communicate with other devices via network 211. Alternatively, the local computing device 206 may be a stationary or standalone device, such as a stationary base station including, for example, modem and/or router capability, a desktop or laptop computer using an executable program to communicate information between the cardiac pacing and diagnosis device 220 and the remote computing system 208 via a radio module or a USB dongle. Biometric data may be communicated between the local computing device 206 and the cardiac pacing and diagnosis device 220 using a short-range wireless technology standard (e.g., Bluetooth, Wi-Fi, ZigBee, Z-wave and other short-range wireless standards) via the short-range wireless network 210, such as a local area network (LAN) (e.g., a personal area network (PAN)). In some embodiments, the local computing device 206 may also be configured to display the observed/obtained patient electrical signals and information associated with the acquired patient electrical signals, as described in more detail herein.

In some embodiments, the remote computing system 208 may be configured to receive at least one of the monitored patient biometrics and information associated with the monitored patient via network 211, which is a long-range network. For example, if the local computing device 206 is a mobile phone, network 211 may be a wireless cellular network, and information may be communicated between the local computing device 206 and the remote computing system 208 via a wireless technology standard, such as any of the wireless technologies mentioned above. As described in more detail herein, the remote computing system 208 may be configured to provide (e.g., visually display and/or aurally provide) the at least one of the patient biometrics and the associated information to a medical professional, a physician, a healthcare professional, or the like.

In FIG. 2, the network 210 is an example of a short-range network (e.g., local area network (LAN), or personal area network (PAN)). Information may be sent, via short-range network 210, between the cardiac pacing and diagnosis device 220 and the local computing device 206 using any one of various short-range wireless communication protocols, such as Bluetooth, Wi-Fi, Zigbee, Z-Wave, near field communications (NFC), ultraband, Zigbee, or infrared (IR).

The network 211 may be a wired network, a wireless network or include one or more wired and wireless networks, such as an intranet, a local area network (LAN), a wide area network (WAN), a metropolitan area network (MAN), a direct connection or series of connections, a cellular telephone network, or any other network or medium capable of facilitating communication between the local computing device 206 and the remote computing system 208. Information may be sent, via the network 211 using any one of various long-range wireless communication protocols (e.g., TCP/IP, HTTP, 3G, 4G/LTE, or 5G/New Radio). Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology. Additionally, several networks may work alone or in communication with each other to facilitate communication in the network 211. In some instances, the remote computing system 208 may be implemented as a physical server on the network 211. In other instances, the remote computing system 208 may be implemented as a virtual server a public cloud computing provider (e.g., Amazon Web Services (AWS)®) of the network 211.

In operation, the cardiac pacing and diagnosis device 220, utilizing the cardiac pacing and diagnosis software, observes/obtains biometric data of the patient 201 (e.g., electrical signals, blood pressure, temperature, blood glucose level or other biometric data) from the patient biometric sensor 221 and/or receives at least a portion of the biometric data representing any acquired patient biometrics and additional information (e.g., the diagnosis information) associated with any acquired patient biometrics from the one or more other patient biometric diagnosis devices. The cardiac pacing and diagnosis software is a processor executable code or software that is necessarily rooted in process operations by, and in processing hardware of, the cardiac pacing and diagnosis device 220 to provide a method for analyzing a specific region or focal point of heart tissue in response to the pacing. According to an embodiment, the cardiac pacing and diagnosis software of the cardiac pacing and diagnosis device 220 provides specific pacing and capturing operations that involve a multi-step manipulation of electrical signals with respect to the heart tissue to understand an electrophysiology of the heart tissue with more precision. The cardiac pacing and diagnosis device 220 may employ the cardiac pacing and diagnosis software to process data, including the obtained/observed/acquired biometric data as well as any biometric data received from the one or more other patient biometric diagnosis devices. For example, when processing data in this regard, the cardiac pacing and diagnosis software includes a neural network that is used to learn latent representations (or data codings) in an unsupervised manner from the biometric data. Further, the cardiac pacing and diagnosis software learns to detect specific data by training the neural network.

The cardiac pacing and diagnosis device 220 may continually or periodically monitor, store, process, and communicate, via network 210, any number of various patient biometrics (e.g., the acquired biometric data). As described herein, examples of patient biometrics include electrical signals (e.g., ECG signals and brain biometrics), blood pressure data, blood glucose data, and temperature data. The patient biometrics may be monitored and communicated for treatment across any number of various diseases, such as cardiovascular diseases (e.g., arrhythmias, cardiomyopathy, and coronary artery disease) and autoimmune diseases (e.g., type I and type II diabetes).

The patient biometric sensor 221 may include, for example, one or more transducers configured to convert one or more environmental conditions into an electrical signal, such that different types of biometric data are observed/obtained/acquired. For example, the patient biometric sensor 221 may include one or more of an electrode (e.g., the electrodes 151 of FIG. 1), a temperature sensor (e.g., thermocouple), a blood pressure sensor, a blood glucose sensor, a blood oxygen sensor, a pH sensor, an accelerometer, and a microphone.

The processor 222, in executing the cardiac pacing and diagnosis software, may be configured to receive, process, and manage, biometric data acquired by the patient biometric sensor 221, and communicate the biometric data to the memory 224 for storage and/or across the network 210 via the transceiver 225. Data from one or more other cardiac pacing and diagnosis device 220 may also be received by the processor 222 through the transceiver 225, as described in more detail herein. Also, as described in more detail herein, the processor 222 may be configured to respond selectively to different tapping patterns (e.g., a single tap or a double tap) received from the UI sensor 223 (e.g., a capacitive sensor therein), such that different tasks of a patch (e.g., acquisition, storing, or transmission of data) may be activated based on the detected pattern. In some embodiments, the processor 222 can generate audible feedback with respect to detecting a gesture.

The UI sensor 223 includes, for example, a piezoelectric sensor or a capacitive sensor configured to receive a user input, such as a tapping or touching. For example, UI sensor 223 may be controlled to implement a capacitive coupling, in response to tapping or touching a surface of the cardiac pacing and diagnosis device 220 by the patient 201. Gesture recognition may be implemented via any one of various capacitive types, such as resistive capacitive, surface capacitive, projected capacitive, surface acoustic wave, piezoelectric and infra-red touching. Capacitive sensors may be disposed at a small area or over a length of the surface, such that the tapping or touching of the surface activates the monitoring device.

The memory 224 is any non-transitory tangible media, such as magnetic, optical, or electronic memory (e.g., any suitable volatile and/or non-volatile memory, such as random-access memory or a hard disk drive). The memory 224 stores the cardiac pacing and diagnosis software for execution by the processor 222.

The transceiver 225 may include a separate transmitter and a separate receiver. Alternatively, the transceiver 225 may include a transmitter and receiver integrated into a single device.

According to an embodiment, the cardiac pacing and diagnosis device 220 may be an apparatus that is internal to a body of the patient 201 (e.g., subcutaneously implantable). The cardiac pacing and diagnosis device 220 may be inserted into the patient 201 via any applicable manner including orally injecting, surgical insertion via a vein or artery, an endoscopic procedure, or a lap aroscopic procedure. According to an embodiment, the cardiac pacing and diagnosis device 220 may be an apparatus that is external to the patient 201. For example, as described in more detail herein, the cardiac pacing and diagnosis device 220 may include an attachable patch (e.g., that attaches to a patient's skin). According to an embodiment, a cardiac pacing and diagnosis device 220 may include both components that are internal to the patient and components that are external to the patient. While a single cardiac pacing and diagnosis device 220 is shown in FIG. 2, example systems may include a plurality of patient biometric diagnosis devices. For instance, the cardiac pacing and diagnosis device 220 may be in communication with one or more other patient biometric diagnosis devices. Additionally or alternatively, the one or more other patient biometric diagnosis device may be in communication with the network 210 and other components of the cardiac pacing and diagnosis system 200.

Figure 3:
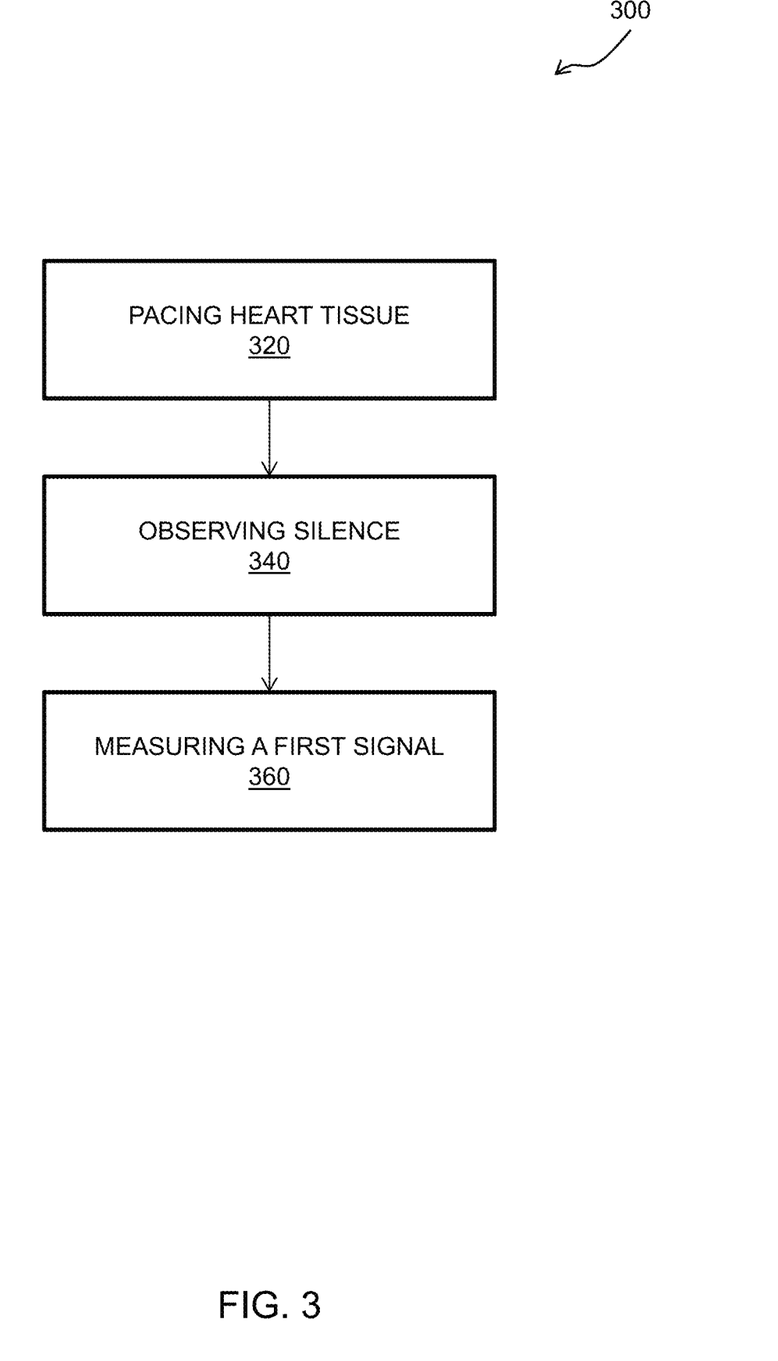
FIG. 3 illustrates a diagram of a method according to one or more embodiments.

FIG. 3 illustrates diagrams of a method 300 (performed in the cardiac pacing and diagnosis apparatus 100 of FIG. 1 and/or the cardiac pacing and diagnosis system 200 of FIG. 2) according to one or more embodiments. The method 300 addresses a need to observe large focal points of heart tissue so that an origin of a source can be understood.

The method begins at block or step 320, where a plurality of electrodes of a catheter (e.g., the electrodes 151 of the catheter 141) paces a heart tissue with a plurality of pulses. Note that each of the plurality of electrodes provides a pulse of the plurality of pulses at one particular, isolated region of the heart tissue. Each of the plurality of pulses can be paced together and at the same time (e.g., in unison) at an isolated section of the heart tissue (e.g., at a same specified focal point). For example, pacing can include a chain of stimulus or an increase of current (from pace to pace) to capture tissue with all the electrodes together, by trying to synchronize the tissue under the electrodes and listening thereafter. The catheter can be a mesh, balloon, or spoon catheter as described herein.

At block or step 340, the plurality of electrodes of the catheter observes a period of electrophysiological repolarization (or period of inactivity of the atrial tissue and that reactivation is impossible) for the heart tissue caused by the pacing. That is, the pacing itself by the multiple electrodes at one focal point generates the period of inactivity of the atrial tissue. The period of electrophysiological repolarization can include a time period when the heart tissue does not produce an activity pattern.

At block or step 360, the plurality of electrodes of the catheter measures an electrical signal within the heart tissue after the period of electrophysiological repolarization. As the pacing at the same specified focal point of the heart tissue occurs in unison and as the pacing is followed by a period of inactivity, the measured electrical signal indicates a first portion of the heart tissue to respond. In this way, the heart tissue or a focal point of the heart tissue can be analyzed and evaluate. In accordance with one or more embodiment, the plurality of electrodes of the catheter can further measure a progress of returning activity patterns after the electrical signal is measured in the heart tissue. In turn, cardiac pacing and diagnosis software (e.g., the cardiac pacing and diagnosis software of the cardiac pacing and diagnosis device 220 of FIG. 2) can isolate and analyze focal points of interest within the heart tissue under the electrode based on the progress of the returning activity patterns.

The technical effects and benefits of the method 300 include enabling the cardiac physician to capture a large area (of the heart 120 of FIG. 1) at once, so that it is possible to understand an electrophysiology of the heart tissue with more precision.

Figure 4:
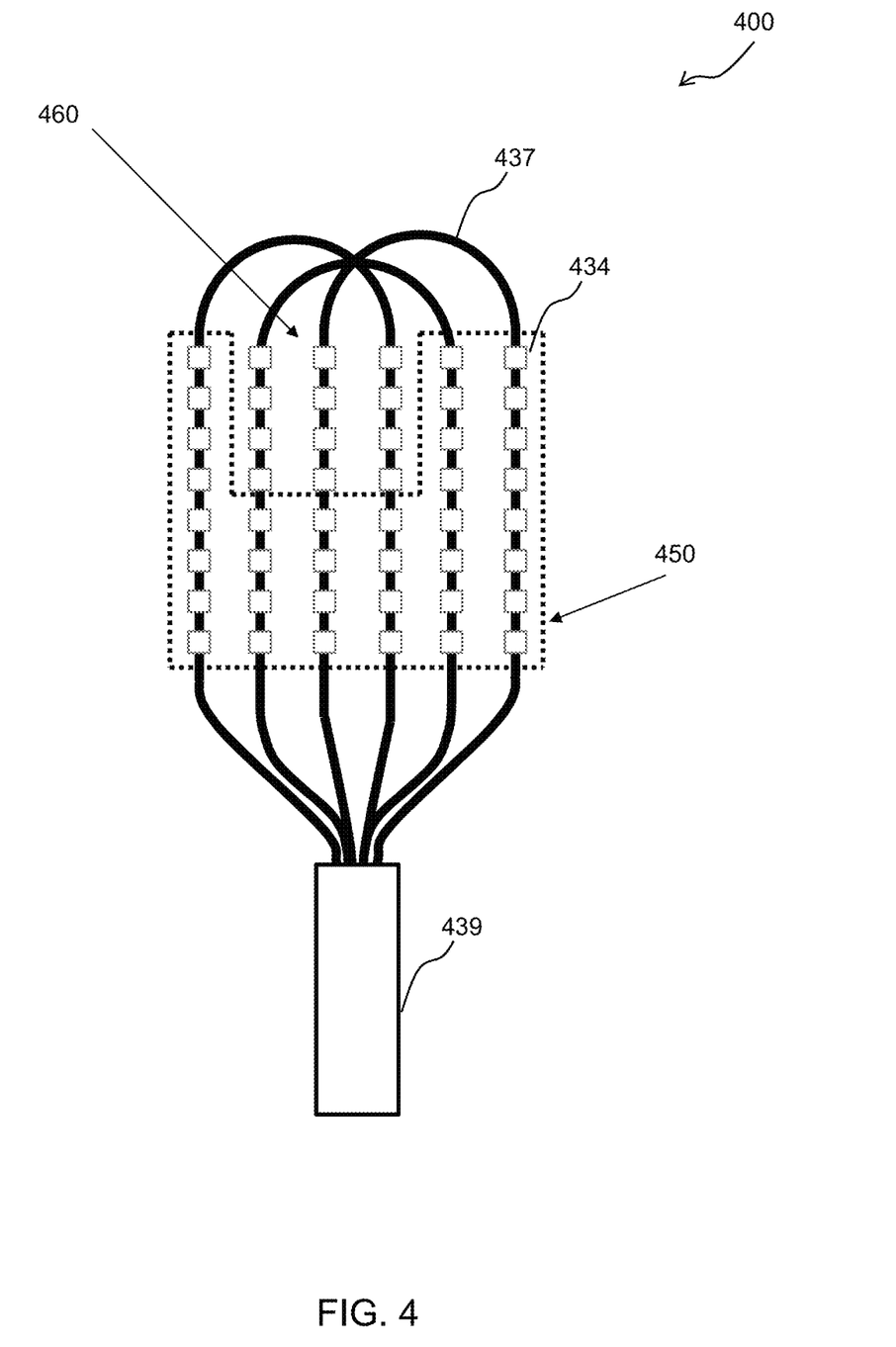
FIG. 4 illustrates an example of a catheter one or more embodiments.

FIG. 4 illustrates an example of a catheter 400 one or more embodiments. The catheter 400 can be a mesh, balloon, or spoon catheter having a plurality of electrodes 434, such as at least forty electrodes. As shown, the plurality of electrodes can include exactly 48 electrodes located across or dispersed on multiple spines 437. Using such a number of electrodes 434 spread across a wide area by the spines 437 allows the capturing a large area at once. According to embodiments, the multiple spines 437 move through the sheath 439 in a collapsed state and may be then expanded once within the patient (e.g., the patient 125 of FIG. 1).

Electrical activity at any focal point in the heart may be typically measured by advancing the catheter 400, contacting the heart tissue with the catheter 400, and acquiring data at that point. Contacting the heart tissue includes utilizing the electrodes 434 for signal analysis by pacing together, in unison, each of the electrodes 434 at the same time at the region of interest to generate a period of inactivity at the given region.

According to one or more embodiments, the activation of the electrodes 434 can vary by number and by location, such as by pacing from any electrode to any electrode or from all electrodes to a further away larger electrode. In an embodiment, using results from a prior pacing, a decreased number of electrodes can be activated at the same time to capture a smaller area. In an embodiment, using results from a prior pacing, a select number of electrodes around a specific location can be activated at the same time to measure correlations of ventricle activity. That is, based on a desired number and/or location, a particular grouping of pulses can be used to manipulate the period of electrophysiological repolarization. For instance, as shown in FIG. 4, an electrode subset 450 can be chosen by the cardiac pacing and diagnosis software to implement the particular grouping of pulses. In this regard, the remaining electrodes 460 are left unused with respect to the pacing.

Figure 5:
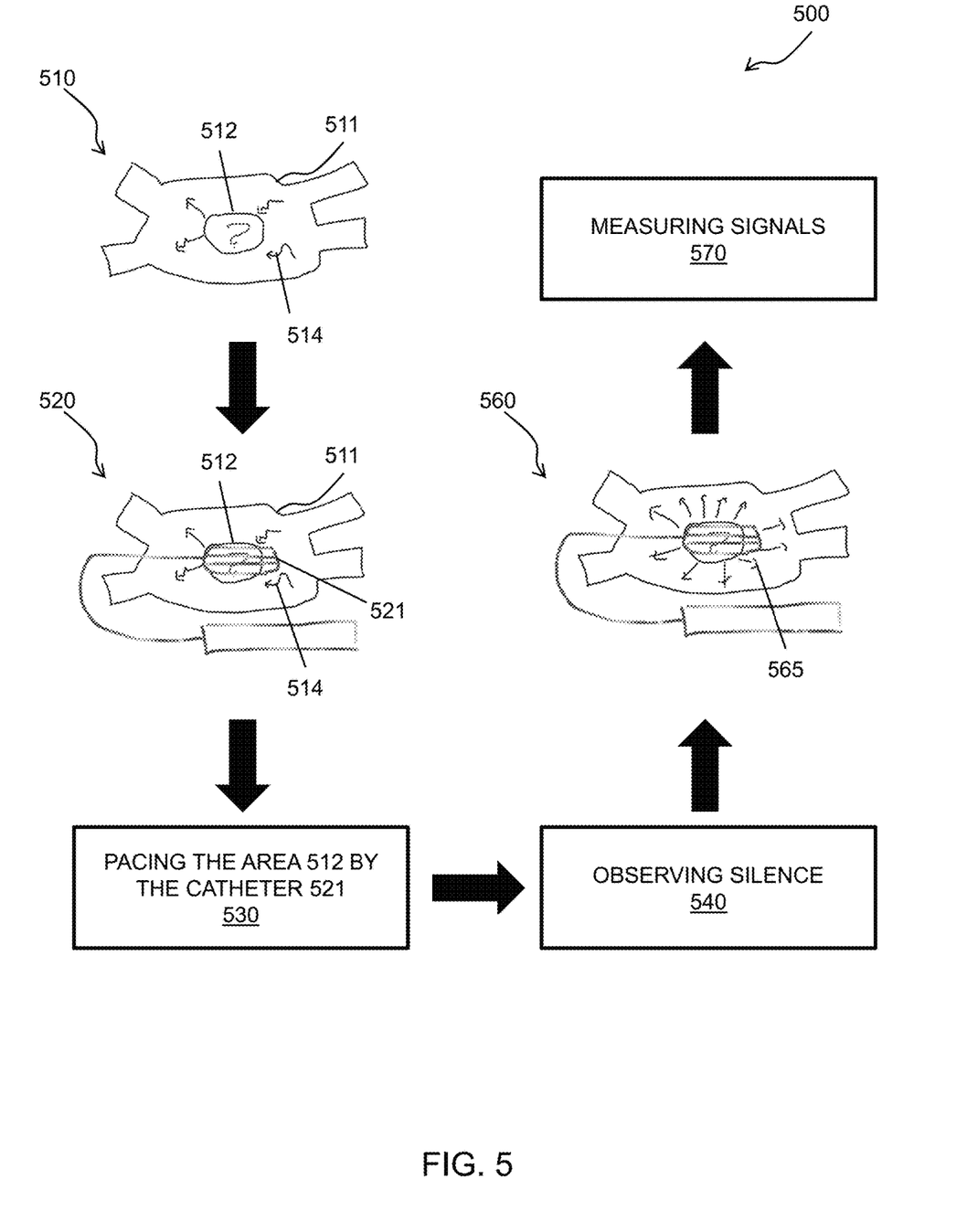
FIG. 5 illustrates a diagram of a method according to one or more embodiments.

FIG. 5 illustrates block diagrams of a method 500 (performed in the cardiac pacing and diagnosis apparatus 100 of FIG. 1 and/or the cardiac pacing and diagnosis system 200 of FIG. 2) according to one or more embodiments. The method 500 addresses a need to observe large focal points of heart tissue so that an origin of a source can be understood.

Generally, during AF, there is not repeatable pattern of wave front activations. Note that AF is a result of many causes, which are still debated. That is, while some researchers identify rotors as a cause, others do not (e.g., identify different focal sources). Rotors and focal sources may be treated differently. In any case, it is important to understand the AF cause and what heart tissue areas are involved to provide the best treatment and positively change the procedure outcome. The method 500 provides a mechanism to understand whether some heart regions have a source using pacing from multiple electrodes. The image 510 generally shows an outline of left atria 511 from a patient back prospective. The image 510 illustrates an area 512, which may be scar or inactive.

Assuming a physician (e.g., medical professional 115 of FIG. 1) suspects that this area 512 is important with the tachycardia and that possibly there is a focal source coming from that area, the physician is still facing a problem that the physician cannot really observe that source as colliding waves 514 are entering the area 512 and generating unorganized repolarization of the heart tissue. This unorganized repolarization is a known condition that sustains the AF regardless the reason causes noted herein. Conventionally, the physician would consider shocking the heart to get it out of the AF condition, to "reset" the heart cell, and to provide opportunity for the sinus rhythm to take control (in many cases this is unfeasible, such as in AFIB the patient would revert immediately to AFIB).

Alternatively, as shown by an image 520, a catheter 521 is placed over this area 512. The catheter 521 can be a mesh, balloon, or spoon catheter as described herein.

At block 530, electrodes of the catheter 421 (e.g., the electrodes 151 of the catheter 141) pace the area 512 with a plurality of pulses. Note that each of the plurality of electrodes provides a pulse to the area 512 of the left atria 511. Each of the plurality of pulses can be paced together and at the same time (e.g., in unison) the area 512 of the left atria 511 (e.g., at a same specified focal point). It is possible to pace all locations of the area 512 of the left atria 511 or just an isolated section of the area 512 of the left atria 511 based on how the diagnosis system selects and groups the plurality of electrodes.

At block 540, the plurality of electrodes of the catheter 521 observes a period of electrophysiological repolarization (or period of inactivity of the atrial tissue and that reactivation is impossible) for the area 512 of the left atria 511 caused by the pacing. That is, the pacing itself by the multiple electrodes at one focal point generates the period of inactivity of the atrial tissue.

By pacing from all the electrodes at once, as shown in an image 560, the method 500 essentially generates a specific region where a wave front 565 is (almost) unified, and importantly eliminates other waves from entering this region until a refractory period of this region returns. This time allows the diagnosis system time to listen for anything coming from within this region (i.e., whether cells in this tissue patch under the electrode behave as a source). In turn, at block 570, the plurality of electrodes of the catheter 521 measures an electrical signal (in mV) within the area 512 of the left atria 511 (e.g., the diagnosis system identifies and analyzes the focal points of interest and how the wave propagates across the region). Note that any activity that comes from within the area 512 can be further used as a target for ablation.

Figure 6:
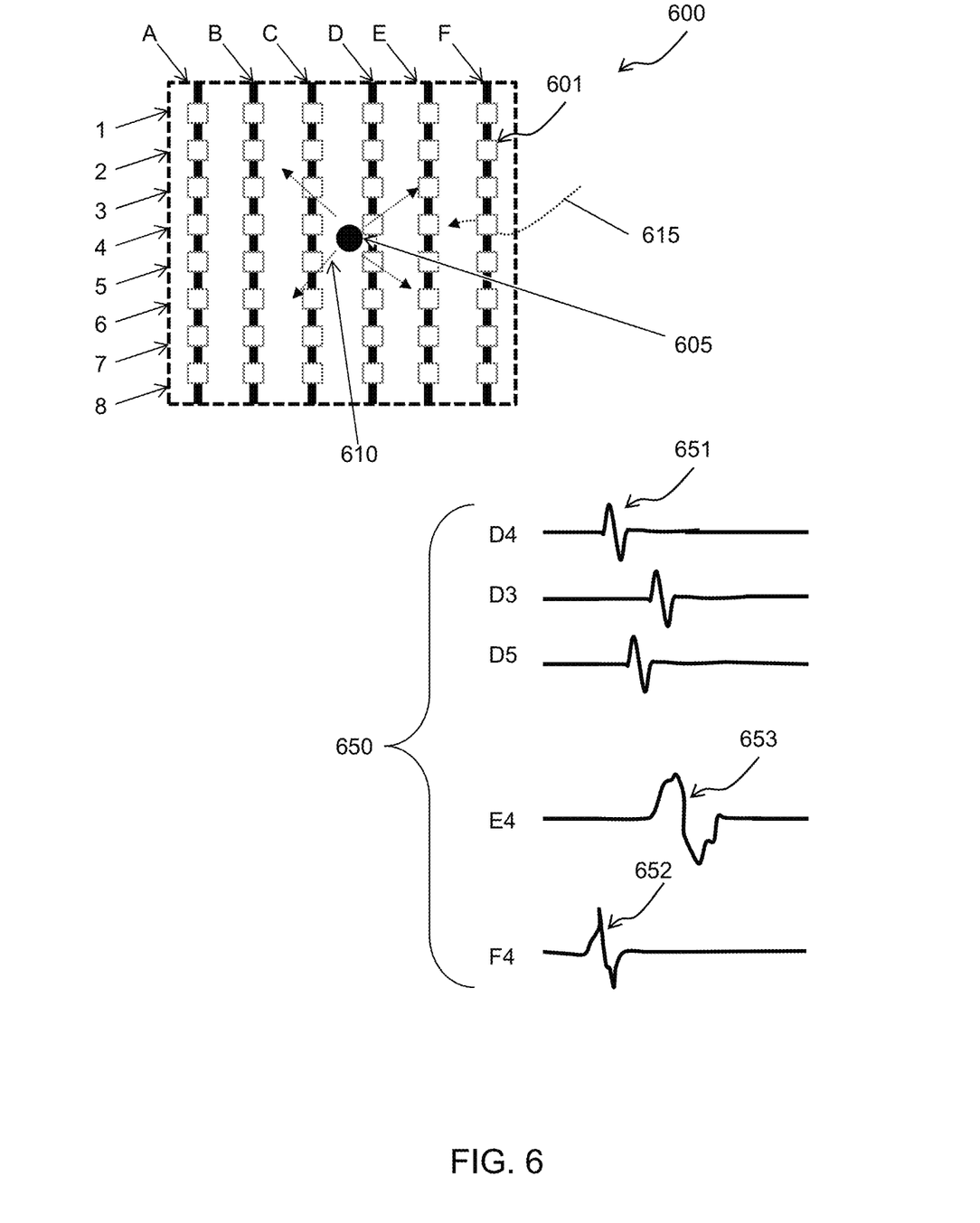
FIG. 6 illustrates an example operation of a catheter and a method according to one or more embodiments.

FIG. 6 illustrates an example operation 600 of a catheter (e.g., the catheter 400) and a method (e.g., the method 500) according to one or more embodiments. As shown in the example operation 600, electrodes 601 are arranged according to a grid with a first direction being designated by letter A-F and a second direction being designated by number 1-8. The grid is aligned with an area of tissue that is suspected to include a source 605. In turn, after a period of electrophysiological repolarization, a wave front 610 propagates from the source 605 and is detected by each of the electrodes 601. In parallel, an external wave 615 enters the area of tissue that is also detected by the electrodes 601.

As shown in the measurements 650, the electrodes D4, D3, and D5 detect the wave front 610 at different times. Note that the morphology 651 represents the source 605. Further, the electrode F4 detects (note the morphology 652) the external wave 615, while the electrode E4 detects (note the morphology 653) a combination of the morphologies 651 and 652. Because of the universal pacing by the grid, the external wave 615 can be ignored and/or subtracted out of the measurements. Importantly, following the signal propagation sequence of the electrodes (and possibly their morphology too), it would be possible to understand that a focal source is present under the electrode patch.

The technical effects and benefits of the method 500 include enabling the cardiac physician to capture a large area (of the heart 120 of FIG. 1) at once, so that it is possible to understand an electrophysiology of the heart tissue with more precision. For example, depending on a catheter size and electrode coverage, a large area (larger that a single pacing) can equate to an approximate size of 2.5×2.5 cm. In contrast, an area size of the single pacing (which is related to related to electrode size and position) from one electrode would not synchronize the region at the same time, but rather mix advancing waves outside the tissue due to the AF.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although features and elements are described above in particular combinations, one of ordinary skill in the art will appreciate that each feature or element can be used alone or in any combination with the other features and elements. In addition, the methods described herein may be implemented in a computer program, software, or firmware incorporated in a computer-readable medium for execution by a computer or processor. A computer readable medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire Examples of computer-readable media include electrical signals (transmitted over wired or wireless connections) and computer-readable storage media. Examples of computer-readable storage media include, but are not limited to, a register, cache memory, semiconductor memory devices, magnetic media such as internal hard disks and removable disks, magneto-optical media, optical media such as compact disks (CD) and digital versatile disks (DVDs), a random access memory (RAM), a read-only memory (ROM), an erasable programmable read-only memory (EPROM or Flash memory), a static random access memory (SRAM), and a memory stick. A processor in association with software may be used to implement a radio frequency transceiver for use in a terminal, base station, or any host computer.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The descriptions of the various embodiments herein have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
pacing, by a plurality of electrodes of a catheter, a heart tissue with a plurality of pulses;
detecting, by the plurality of electrodes of the catheter, a period of electrophysiological repolarization for the heart tissue caused by the pacing;
measuring, by the plurality of electrodes of the catheter, an electrical signal within the heart tissue after the period of electrophysiological repolarization; and
measuring, by the plurality of electrodes of the catheter, an activity pattern of returning electrical signals after the electrical signal is measured in the heart tissue, the returning electrical signals propagating from the heart tissue.

2. The method of claim 1, wherein each electrode of the plurality of electrodes provides a pulse of the plurality of pulses.

3. The method of claim 1, wherein the period of electrophysiological repolarization comprises a time period when the heart tissue is in a refractory period.

4. The method of claim 1, further comprising:
isolating and analyzing focal points of interest within the heart tissue based on the activity pattern across the plurality of electrodes.

5. The method of claim 1, wherein the catheter comprises a mesh, balloon, or spoon catheter.

6. The method of claim 1, wherein the plurality of electrodes comprises at least forty electrodes.

7. The method of claim 1, wherein each pulse of the plurality of pulses are paced together and at a same time.

8. The method of claim 1, wherein the plurality of pulses are paced to control a time between each pacing.

9. The method of claim 1, wherein each of a number or a location of the plurality of pulses is varied to manipulate the period of electrophysiological repolarization.

10. The method of claim 1, wherein an isolated section of the heart tissue is paced.

11. An apparatus comprising:
a catheter comprising a plurality of electrodes; and
a cardiac pacing and diagnosis device comprising a memory storing processor executable instructions of cardiac pacing and diagnosis software, and a processor configured to execute the processor executable instructions of the cardiac pacing and diagnosis software to cause the apparatus to:
pace, by the plurality of electrodes of the catheter, a heart tissue with a plurality of pulses;
detect, by the plurality of electrodes of the catheter, a period of electrophysiological repolarization for the heart tissue caused by the pacing;
measure, by the plurality of electrodes of the catheter, an electrical signal within the heart tissue after the period of electrophysiological repolarization; and
measure, by the plurality of electrodes of the catheter, an activity pattern of returning electrical signals after the electrical signal is measured in the heart tissue, the returning electrical signals propagating from the heart tissue.

12. The apparatus of claim 11, wherein each electrode of the plurality of electrodes provides a pulse of the plurality of pulses.

13. The apparatus of claim 11, wherein the period of electrophysiological repolarization comprises a time period when the heart tissue is in a refractory period.

14. The apparatus of claim 11, wherein the processor is configured to execute the processor executable instructions of the cardiac pacing and diagnosis software to cause the apparatus to:
isolate and analyze focal points of interest within the heart tissue based on the activity pattern across the plurality of electrodes.

15. The apparatus of claim 11, wherein the catheter comprises a mesh, balloon, or spoon catheter.

16. The apparatus of claim 11, wherein the plurality of electrodes comprises at least forty electrodes.

17. The apparatus of claim 11, wherein each of the plurality of pulses are paced together and at the same time.

18. The apparatus of claim 11, wherein the plurality of pulses are paced to control a time between each pacing.

* * * * *

UNITED STATES PATENT AND TRADEMARK OFFICE
CERTIFICATE OF CORRECTION

PATENT NO. : 11,779,770 B2
APPLICATION NO. : 16/938200
DATED : October 10, 2023
INVENTOR(S) : Lior Botzer It is certified that error appears in the above-identified patent and that said Letters Patent is hereby corrected as shown below:

In the Specification

In Column 2, Line 1, delete "one" and insert -- in one --, therefor.
In Column 2, Line 58, delete "side to" and insert -- one side to --, therefor.
In Column 3, Line 39, delete "view a" and insert -- view of a --, therefor.
In Column 4, Line 8, delete "and or" and insert -- and/or --, therefor.
In Column 9, Line 1, delete "a" and insert -- of a --, therefor.
In Column 10, Line 36, delete "lap aroscopic" and insert -- laparoscopic --, therefor.
In Column 11, Line 24, delete "evaluate." and insert -- evaluated. --, therefor.
In Column 11, Line 25, delete "embodiment," and insert -- embodiments, --, therefor.
In Column 11, Line 38, delete "one" and insert -- in one --, therefor.
In Column 11, Line 45, delete "a" and insert -- of a --, therefor.
In Column 12, Line 13, delete "not" and insert -- no --, therefor.
In Column 12, Line 24, delete "patient" and insert -- patient's --, therefor.
In Column 12, Line 25, delete "prospective." and insert -- perspective. --, therefor.
In Column 12, Line 35, delete "the" and insert -- of the --, therefor.
In Column 13, Line 39, delete "that" and insert -- than --, therefor.
In Column 13, Line 42, delete "to related to" and insert -- to --, therefor.
In Column 14, Line 12, delete "wire" and insert -- wire. --, therefor.

Signed and Sealed this
Nineteenth Day of March, 2024

Katherine Kelly Vidal
*Director of the United States Patent and Trademark Office*